United States Patent
Uriel et al.

(10) Patent No.: US 11,247,037 B2
(45) Date of Patent: Feb. 15, 2022

(54) VENTRICULAR FILLING PHASE SLOPE AS AN INDICATOR OF HIGH PULMONARY CAPILLARY WEDGE PRESSURE AND/OR CARDIAC INDEX

(71) Applicant: The University of Chicago, Chicago, IL (US)

(72) Inventors: Nir Uriel, Chicago, IL (US); Jonathan Grinstein, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/082,019

(22) PCT Filed: Mar. 10, 2017

(86) PCT No.: PCT/US2017/021767
§ 371 (c)(1),
(2) Date: Sep. 4, 2018

(87) PCT Pub. No.: WO2017/156386
PCT Pub. Date: Sep. 14, 2017

(65) Prior Publication Data
US 2020/0246524 A1    Aug. 6, 2020

Related U.S. Application Data

(60) Provisional application No. 62/306,418, filed on Mar. 10, 2016.

(51) Int. Cl.
*A61M 60/50* (2021.01)

(52) U.S. Cl.
CPC ..... *A61M 60/50* (2021.01); *A61M 2205/3331* (2013.01)

(58) Field of Classification Search
CPC ............ A61M 1/1086; A61M 2205/3331
See application file for complete search history.

(56) References Cited

U.S. PATENT DOCUMENTS

| | | | |
|---|---|---|---|
| 8,506,470 B2 * | 8/2013 | LaRose | A61M 1/122 600/16 |
| 2011/0202495 A1 * | 8/2011 | Gawlick | G16H 50/20 706/59 |

FOREIGN PATENT DOCUMENTS

WO   WO2015/179921 A1 * 12/2015 .......... A61M 1/1086

OTHER PUBLICATIONS

Garcia, Mario J., et al. "An index of early left ventricular filling that combined with pulsed Doppler peak E velocity may estimate capillary wedge pressure." Journal of the American College of Cardiology 29.2 (1997): 448-454.] (Year: 1997).*

(Continued)

*Primary Examiner* — Gary Jackson
*Assistant Examiner* — Alexander M Eisenberg
(74) *Attorney, Agent, or Firm* — Bell & Manning, LLC

(57) ABSTRACT

A controller is provided to determine a ventricular filling phase slope as an indicator of high pulmonary capillary wedge pressure and/or cardiac index. Flow rate values describing a blood flow rate through a ventricular assist device are received. A ventricular filling phase segment is identified from a portion of the received flow rate values. A slope of the received flow rate values during the identified ventricular filling phase segment is determined. The determined slope is compared to a predetermined threshold value. When the determined slope exceeds the predetermined threshold value based on the comparison, a warning is triggered regarding an elevated pulmonary capillary wedge pressure or a low cardiac index value.

20 Claims, 7 Drawing Sheets

(56) References Cited

OTHER PUBLICATIONS

Lange, Richard A., et al. "Use of pulmonary capillary wedge pressure to assess severity of mitral stenosis: is true left atrial pressure needed in this condition?." Journal of the American College of Cardiology 13.4 (1989): 825-829. (Year: 1989).*

Topalian, Simon, Fredric Ginsberg, and Joseph E. Parrillo. "Cardiogenic shock." Critical care medicine 36.1 (2008): S66-S74. (Year: 2008).*

\* cited by examiner

VENTRICULAR FILLING PHASE SLOPE AS AN INDICATOR OF HIGH PULMONARY CAPILLARY WEDGE PRESSURE AND/OR CARDIAC INDEX

CROSS-REFERENCE TO RELATED APPLICATIONS

The present application is a National Stage Entry of International Application No. PCT/US2017/021767 that was filed Mar. 10, 2017, the entire contents of which are hereby incorporated by reference. International Application No. PCT/US2017/021767 claims the benefit of 35 U.S.C. § 119(e) to U.S. Provisional Patent Application No. 62/306,418 that was filed on Mar. 10, 2016, the entire contents of which are hereby incorporated by reference.

BACKGROUND

Flow waveforms may be determined by a ventricular assist device (VAD) such as a left ventricular assist device (LVAD). The flow waveforms can be used to evaluate the properties and performance of the VAD.

SUMMARY

In another example embodiment, a computer-readable medium is provided having stored thereon computer-readable instructions that, when executed by a computing device, cause the computing device to determine a ventricular filling phase slope as an indicator of high pulmonary capillary wedge pressure and/or cardiac index. Flow rate values describing a blood flow rate through a ventricular assist device are received. A ventricular filling phase segment is identified from a portion of the received flow rate values. A slope of the received flow rate values during the identified ventricular filling phase segment is determined. The determined slope is compared to a predetermined threshold value. When the determined slope exceeds the predetermined threshold value based on the comparison, a warning is triggered regarding an elevated pulmonary capillary wedge pressure or a low cardiac index value.

In yet another example embodiment, a controller is provided. The controller includes, but is not limited to, a processor and a computer-readable medium operably coupled to the processor. The computer-readable medium has instructions stored thereon that, when executed by the controller, cause the controller to determine the ventricular filling phase slope as an indicator of high pulmonary capillary wedge pressure and/or cardiac index.

In an example embodiment, a method of determining a ventricular filling phase slope as an indicator of high pulmonary capillary wedge pressure and/or cardiac index is provided.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

DETAILED DESCRIPTION

Figure 1:
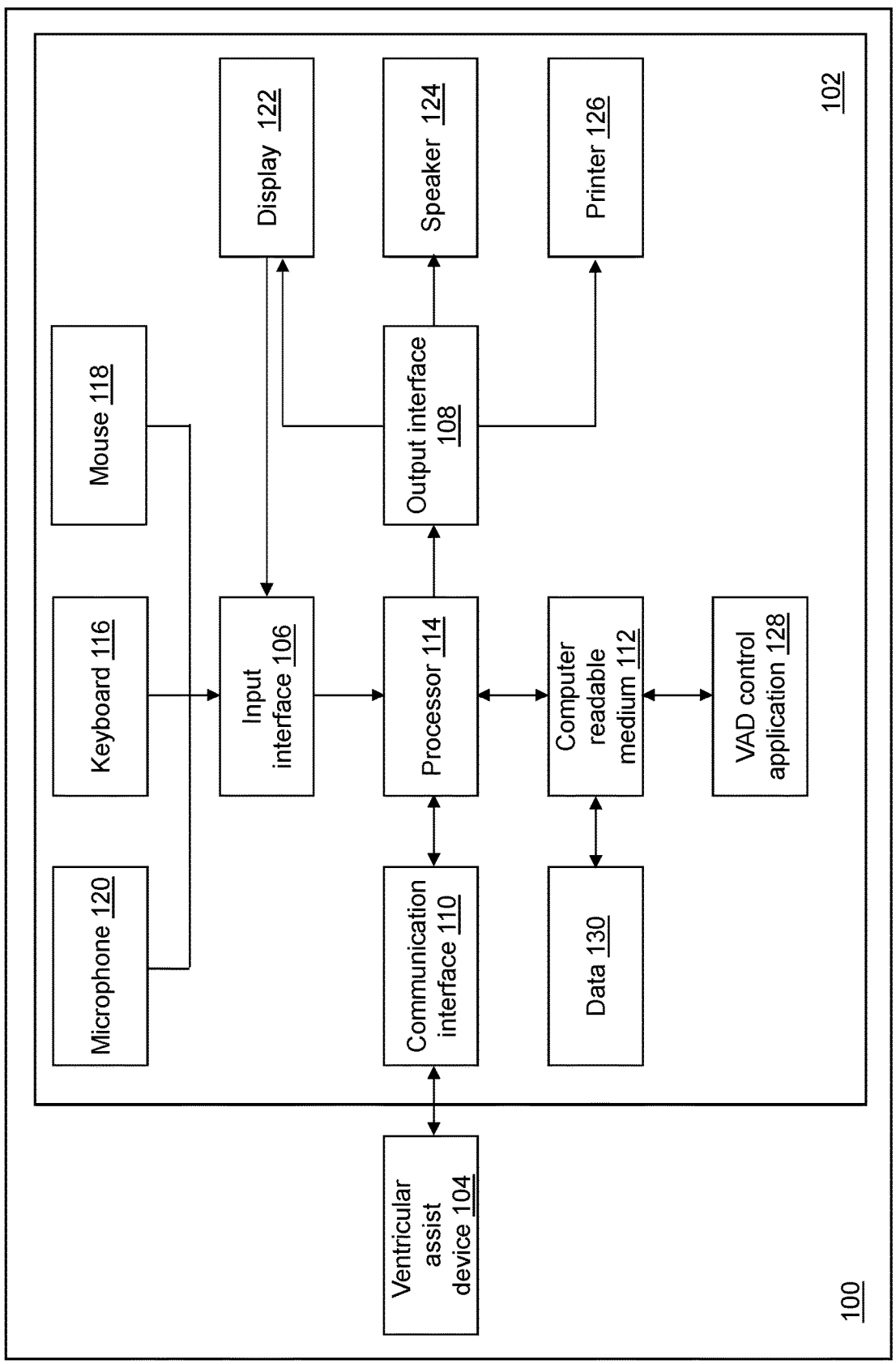
FIG. 1 depicts a block diagram of a VAD operating system in accordance with an illustrative embodiment.

Referring to FIG. 1, a block diagram of a ventricular assist device (VAD) operating system 100 is shown in accordance with an illustrative embodiment. VAD operating system 100 may include a controller 102 and a VAD 104. In an illustrative embodiment, VAD 104 may be a left VAD such as the HVAD® produced by HeartWare headquartered in Framingham, Mass., USA. VAD 104 takes over some or all of a pumping function of a heart of a subject. VAD 104 includes a pump positioned inside a chest of the subject and connected directly to the heart of the subject. VAD 104 may pump blood from a left side of the heart into the aorta. The blood exits the pump in a continuous stream through action of an impeller that is continuously rotated within a cavity. VAD 104 is controlled by controller 102, which is a computing device. In an alternative embodiment, VAD 104 is a right VAD coupled to the right ventricle and pulmonary artery.

Controller 102 may include an input interface 106, an output interface 108, a communication interface 110, a computer-readable medium 112, a processor 114, a VAD control application 128, and data 130. Fewer, different, and/or additional components may be incorporated into controller 102.

Input interface 106 provides an interface for receiving information into controller 102 as understood by those skilled in the art. Input interface 106 may interface with various input technologies including, but not limited to, a keyboard 116, a mouse 118, a microphone 120, a display 122, a track ball, a keypad, one or more buttons, etc. The same interface may support both input interface 106 and output interface 108. For example, display 122 comprising a touch screen provides user input and presents output to the user. Controller 102 may have one or more input interfaces that use the same or a different input interface technology. The input interface technology further may be accessible by controller 102 through communication interface 110.

Output interface 108 provides an interface for outputting information for from controller 102. For example, output interface 108 may interface with various output technologies including, but not limited to, display 122, a speaker 124, a printer 126, etc. Controller 102 may have one or more output interfaces that use the same or a different output interface technology. The output interface technology further may be accessible by controller 102 through communication interface 110.

Communication interface 110 provides an interface for receiving and transmitting data between devices using various protocols, transmission technologies, and media as understood by those skilled in the art. Communication interface 110 may support communication using various transmission media that may be wired and/or wireless. Controller 102 may have one or more communication interfaces that use the same or a different communication interface technology. For example, controller 102 may support communication using an Ethernet port, a Bluetooth antenna, a telephone jack, a USB port, etc. Data and messages may be transferred between controller 102 and VAD 104 using communication interface 110.

Computer-readable medium 112 is an electronic holding place or storage for information so the information can be accessed by processor 114 as understood by those skilled in the art. Computer-readable medium 112 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. Controller 102 may have one or more computer-readable media that use the same or a different memory media technology. For example, computer-readable medium 112 may include different types of computer-readable media that may be organized hierarchically to provide efficient access to the data stored therein as understood by a person of skill in the art. As an example, a cache may be implemented in a smaller, faster memory that stores copies of data from the most frequently/recently accessed main memory locations to reduce an access latency. Controller 102 also may have one or more drives that support the loading of a memory media such as a CD, DVD, an external hard drive, etc. One or more external hard drives further may be connected to controller 102 using communication interface 110.

Processor 114 executes instructions as understood by those skilled in the art. The instructions may be carried out by a special purpose computer, logic circuits, or hardware circuits. Processor 114 may be implemented in hardware and/or firmware. Processor 114 executes an instruction, meaning it performs/controls the operations called for by that instruction. The term "execution" is the process of running an application or the carrying out of the operation called for by an instruction. The instructions may be written using one or more programming language, scripting language, assembly language, etc. Processor 114 operably couples with input interface 106, with output interface 108, with communication interface 110, and with computer-readable medium 112 to receive, to send, and to process information. Processor 114 may retrieve a set of instructions from a permanent memory device and copy the instructions in an executable form to a temporary memory device that is generally some form of RAM. Controller 102 may include a plurality of processors that use the same or a different processing technology.

VAD control application 128 performs operations associated with receiving and processing blood flow data from VAD 104 to determine a status of the heart, a status of VAD 104, and/or new control parameter settings for VAD 104. Some or all of the operations described herein may be embodied in VAD control application 128. The operations may be implemented using hardware, firmware, software, or any combination of these methods. Referring to the example embodiment of FIG. 1, VAD control application 128 is implemented in software (comprised of computer-readable and/or computer-executable instructions) stored in computer-readable medium 112 and accessible by processor 114 for execution of the instructions that embody the operations of VAD control application 128. VAD control application 128 may be written using one or more programming languages, assembly languages, scripting languages, etc. VAD control application 128 may be a plug-in to another application that provides additional functionality. Some or all of the operations of VAD control application 128 may be distributed between VAD 104 and controller 102.

VAD control application 128 may be implemented as a Web application. For example, VAD control application 128 may be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

Data 130 may include any type of content represented using any computer-readable format such as binary, alphanumeric, numeric, markup language, etc. Data 130 may be stored using various structures as known to those skilled in the art including a file system, a relational database, a system of tables, a structured query language database, etc. Data 130 may include sensor data captured at a plurality of times. For example, a sensor may capture measures in the form of flow rate signals, pressure signals, infrared signals, radio frequency signals, thermal signals, magnetic field signals, electrical field signals, electromagnetic signals, magnetic resonance signals, optical signals, electrical current signals, electrical voltage signals, sound wave signals, etc. Data 130 further may include statistical values computed from the sensor data.

For illustration, VAD 104 and controller 102 may be connected by a small cable that passes through skin covering an upper abdomen of the subject. Controller 102 monitors and controls operating parameters of the pump of VAD 104, in particular rotation of the impeller, and may provide messages and audible alarms based on various determinations related to the current operational status of VAD 104 and/or the heart to which VAD 104 is attached. In an alternative embodiment, some or all of the elements of controller 102 may be positioned inside a body of the subject while connecting to other elements of controller 102 that are maintained outside the body.

Figure 2:
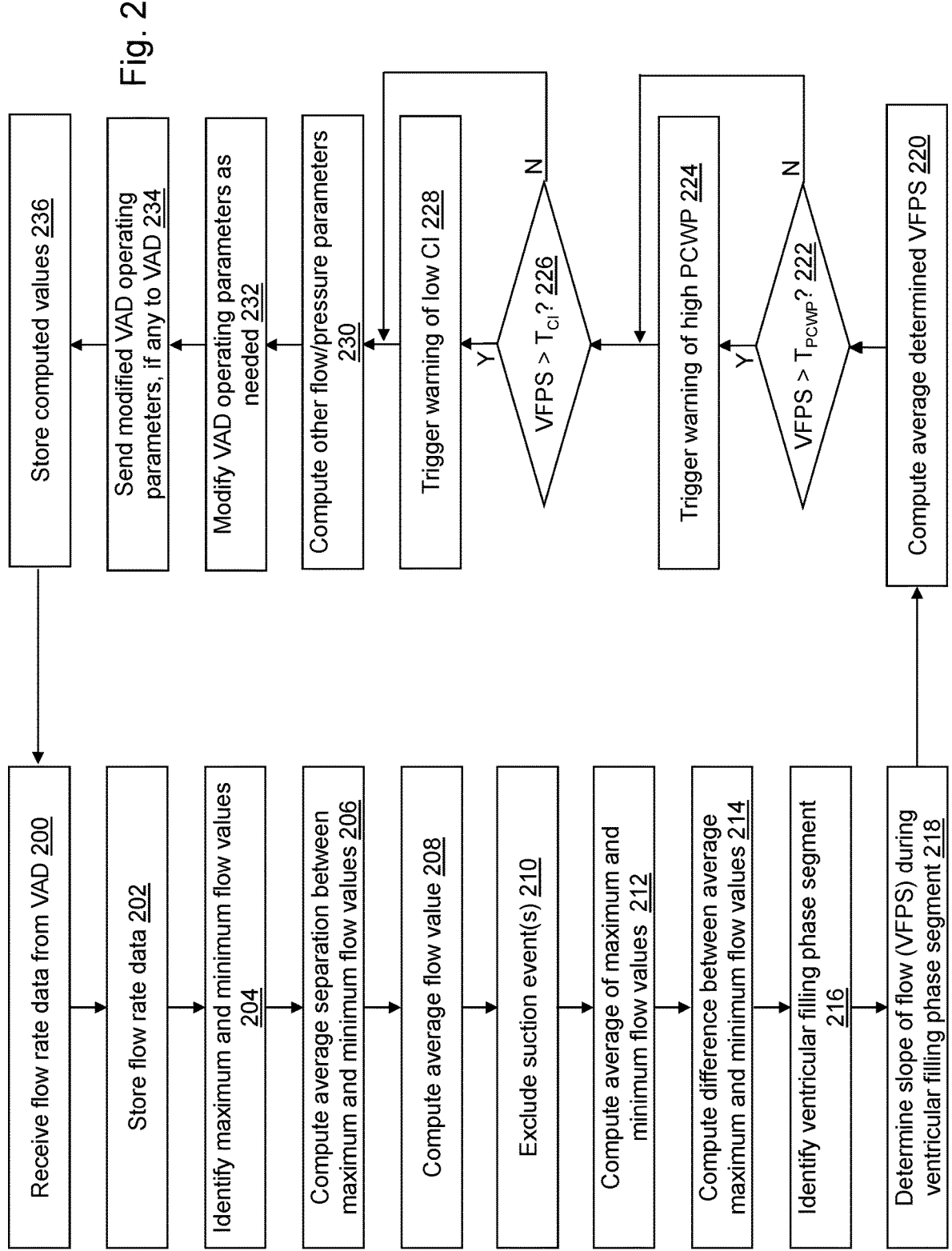
FIG. 2 depicts a flow diagram of example operations performed by a controller of the VAD operating system of FIG. 1 in accordance with an illustrative embodiment.

Referring to FIG. 2, example operations associated with VAD control application 128 are described. Additional, fewer, or different operations may be performed depending on the embodiment. The order of presentation of the operations of FIG. 2 is not intended to be limiting. Although some of the operational flows are presented in sequence, the various operations may be performed in various repetitions, concurrently (in parallel, for example, using threads), and/or in other orders than those that are illustrated. For example, a user may execute VAD control application 128, which causes presentation of a first user interface window, which may include a plurality of menus and selectors such as drop down menus, buttons, text boxes, hyperlinks, etc. associated with VAD control application 128 as understood by a person of skill in the art. The plurality of menus and selectors may be accessed in various orders. An indicator may indicate one or more user selections from a user interface, one or more data entries into a data field of the user interface, one or more data items read from computer-readable medium 112 or otherwise defined with one or more default values, etc. that are received as an input by VAD control application 128.

Figure 3:
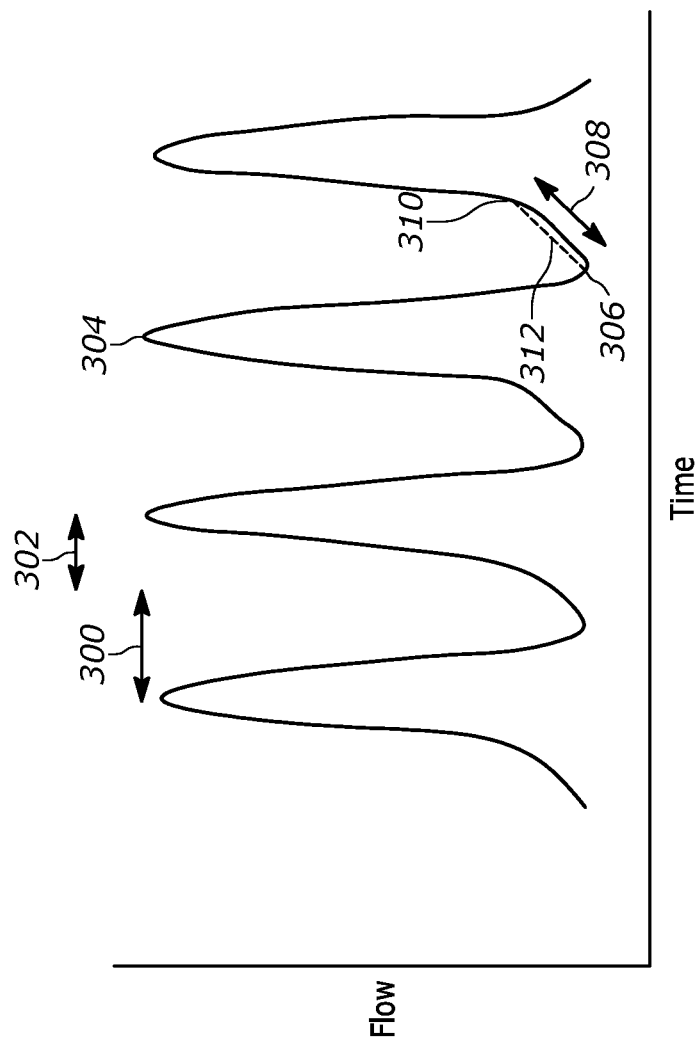
FIG. 3 shows a graph of blood flow as a function of time through a left ventricle of a heart in accordance with an illustrative embodiment.

In an operation 200, blood flow rate data is received from VAD 104 that indicates a rate of blood flow through VAD 104. A flow rate value can be determined in any suitable manner from the blood flow rate data and can be obtained from sensors incorporated within VAD 104, or may be derived from operating characteristics of VAD 104, for example, by monitoring rotation of the impeller as described in U.S. Pat. No. 8,506,470. The flow rate value may be calculated by controller 102 from the received flow rate data or may be received as flow rate values from VAD 104. For illustration, FIG. 3 shows flow rate values as a function of time received from VAD 104. For each heart beat, a diastolic period 300 is followed by a systolic period 302.

Referring again to FIG. 2, in an operation 202, the received flow rate data that includes flow rate values is stored, for example, in computer-readable medium 112 as data 130.

In an operation 204, a maximum flow rate value and a minimum flow rate value are identified for separate cardiac (heartbeat) cycles corresponding to individual heartbeats. Referring again to FIG. 3, a maximum flow rate value 304 and a minimum flow rate value 306 is indicated for a single heartbeat. The maximum flow rate value and the minimum flow rate value may be identified for one or more heartbeat cycles. A number of the heartbeat cycles may be predefined by a user, for example, through a user interface window or as a default value stored in computer-readable medium 112 as data 130.

Referring again to FIG. 2, in an operation 206, an average separation between the maximum flow rate value and the minimum flow rate value is computed. In an operation 208, an average flow rate value is computed based on the received flow rate values. The average may be a time-windowed, running average such that the average is computed over a previous time window. The previous time window may be predefined by a user, for example, through a user interface window or as a default value stored in computer-readable medium 112 as data 130.

In an operation 210, suction events may be removed, for example, as described in WO 2015/179921. In an operation 212, an average maximum flow rate value and an average minimum flow rate value are computed. In an operation 214, a difference between the average maximum flow rate value and the average minimum flow rate value is computed.

In an operation 216, a ventricular filling phase segment is identified for each heart beat using the difference between the average maximum flow rate value and the average minimum flow rate value. For example, the ventricular filling phase segment is defined as the period between a point of least flow and a point a predefined percentage of the average maximum flow rate value is reached though other criteria may be used. The predefined percentage may be predefined by a user, for example, through a user interface window or as a default value stored in computer-readable medium 112 as data 130. For illustration, FIG. 3 indicates a ventricular filling phase segment 308 defined between minimum flow rate value 306 and an intermediate flow rate value 310 that is selected as ~20% of the average maximum flow rate value.

In an operation 218, a slope of the flow rate during the identified ventricular filling phase segment (ventricular filling phase slope (VFPS)) is determined, for example, by fitting a line to the flow rate values during the segment using a method of least squares. For example, a line 312 is computed as a curve fit between minimum flow rate value 306 and an intermediate flow rate value 310, and a slope of line 312 is computed. In an operation 220, an average VFPS may be computed over the one or more heartbeat cycles.

In an operation 222, a determination is made concerning whether or not the determined VFPS is greater than a threshold value $T_{PCWP}$. If the determined VFPS is greater than a threshold value $T_{PCWP}$, processing continues in an operation 224. If the determined VFPS is not greater than a threshold value $T_{PCWP}$, processing continues in an operation 226. In an alternative embodiment, the computed average VFPS may be compared to the threshold value $T_{PCWP}$.

The threshold value $T_{PCWP}$ may be predefined by a user, for example, through a user interface window or as a default value stored in computer-readable medium 112 as data 130. For example, a pulmonary capillary wedge pressure (PCWP) is a pressure measured by wedging a pulmonary catheter with an inflated balloon into a small pulmonary arterial branch. The comparison in operation 222 can be used to indicate when the PCWP is high. For example, a PCWP>20 millimeters of mercury (mmHg) is considered to indicate a presence of acute pulmonary edema. An elevated PCWP has also been used to diagnose a severity of left ventricular failure and mitral stenosis because elevated PCWP strongly suggests failure of left ventricular output.

Figure 4:
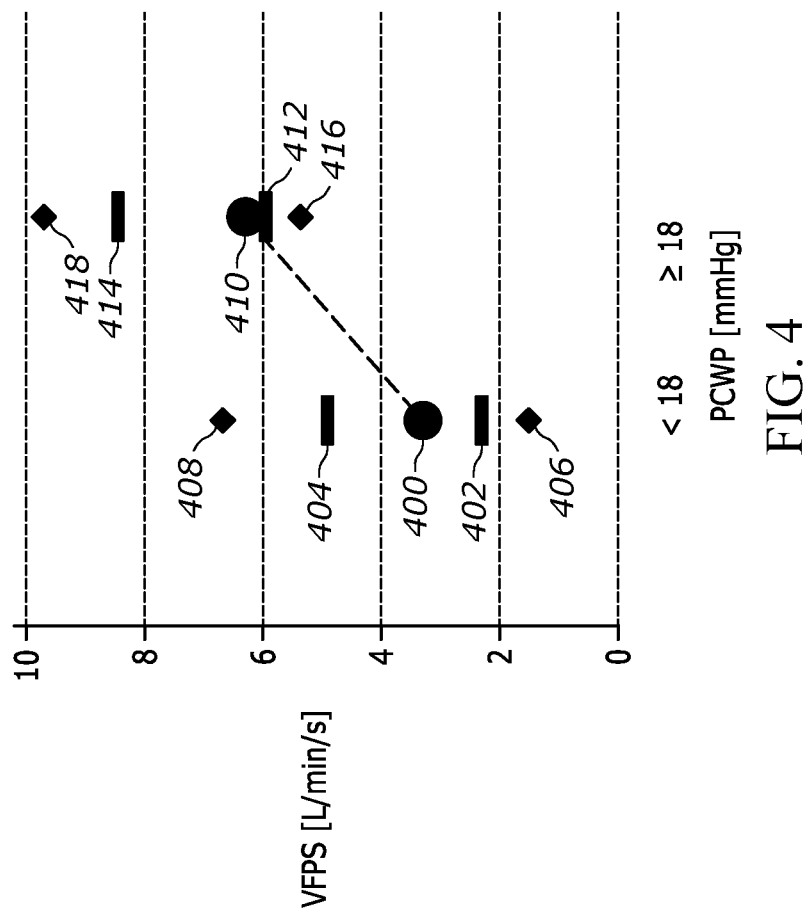
FIG. 4 shows a whisker plot of ventricular filling phase slope versus pulmonary capillary wedge pressure in accordance with an illustrative embodiment.

Referring to FIG. 4, a whisker plot of ventricular filling phase slope versus PCWP<18 mmHg and PCWP≥18 mmHg is shown in accordance with an illustrative embodiment. It was determined that VFPS was significantly higher in patients with PCWP≥18 mmHg than in patients with PCWP<18 mmHg (6.9±1.8 liters per minute per second (L/min/s) vs. 4.7±2.1 L/min/s, p=0.0001). The VFPS values for PCWP<18 mmHg shown in FIG. 4 include a median VFPS value 400, a lower quartile VFPS value 402, an upper quartile VFPS value 404, a lower decile VFPS value 406, and an upper decile VFPS value 408. The VFPS values for PCWP≥18 mmHg shown in FIG. 4 include a median VFPS value 410, a lower quartile VFPS value 412, an upper quartile VFPS value 414, a lower decile VFPS value 416, and an upper decile VFPS value 418.

Figure 5:
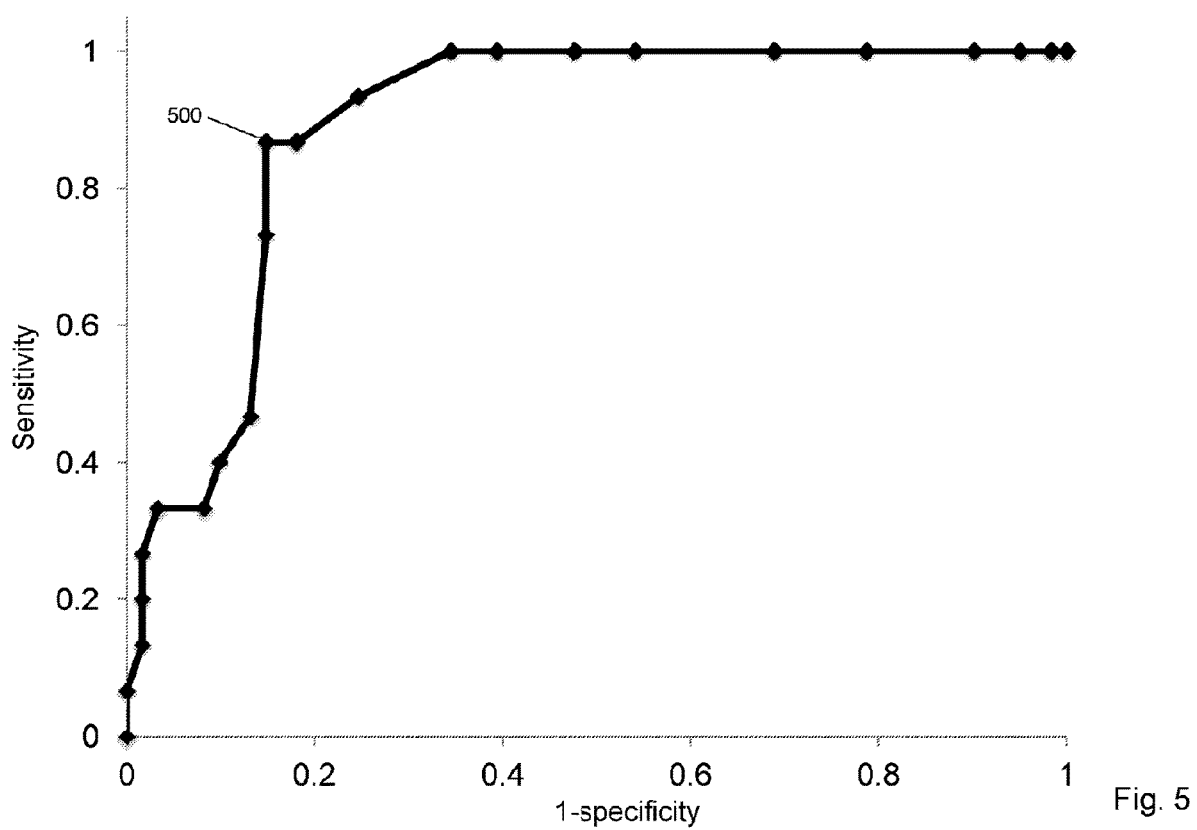
FIG. 5 shows a receiver operating characteristic curve for using a ventricular filling phase slope value to predict a pulmonary capillary wedge pressure greater than 18 mmHg in accordance with an illustrative embodiment.

Referring to FIG. 5, a receiver operating characteristic curve for using VFPS to predict PCWP≥18 mmHg is shown in accordance with an illustrative embodiment. A ventricular filling phase slope threshold 500 (threshold value $T_{PCWP}$) of 5.8 L/min/s predicted a PCWP≥18 mmHg with a sensitivity of 87% and specificity of 85% (area under curve (AUC) =0.9).

In operation 224, a warning is triggered indicating that a high value of PCWP is statistically likely based on the threshold value $T_{PCWP}$. For example, a message may be stored in computer-readable medium 112 as data 130, presented on display 122, printed on printer 126, and/or issued as an audible warning through speaker 124.

In an operation 226, a determination is made concerning whether or not the determined VFPS is greater than a threshold value $T_{CI}$. If the determined VFPS is greater than a threshold value $T_{CI}$, processing continues in an operation 228. If the determined VFPS is not greater than a threshold value $T_{CI}$, processing continues in an operation 230. In an alternative embodiment, the computed average VFPS may be compared to the threshold value $T_{CI}$.

The threshold value TCI may be predefined by a user, for example, through a user interface window or as a default value stored in computer-readable medium 112 as data 130. For example, a cardiac index (CI) is a hemodynamic parameter that relates the cardiac output (CO) from the left ventricle of the heart in one minute to a body surface area thereby relating heart performance to a size of the subject. A normal range of cardiac index in a subject at rest is 2.6-4.2 liters per minute per square meter (L/min/m²). The CI is a useful marker of how well the heart is functioning as a pump by directly correlating the volume of blood pumped by the heart with the subject's body surface area. If the CI falls below 2.2 L/min/m², the patient may be in cardiogenic shock. The comparison in operation 226 can be used to indicate when the CI is low.

Figure 6:
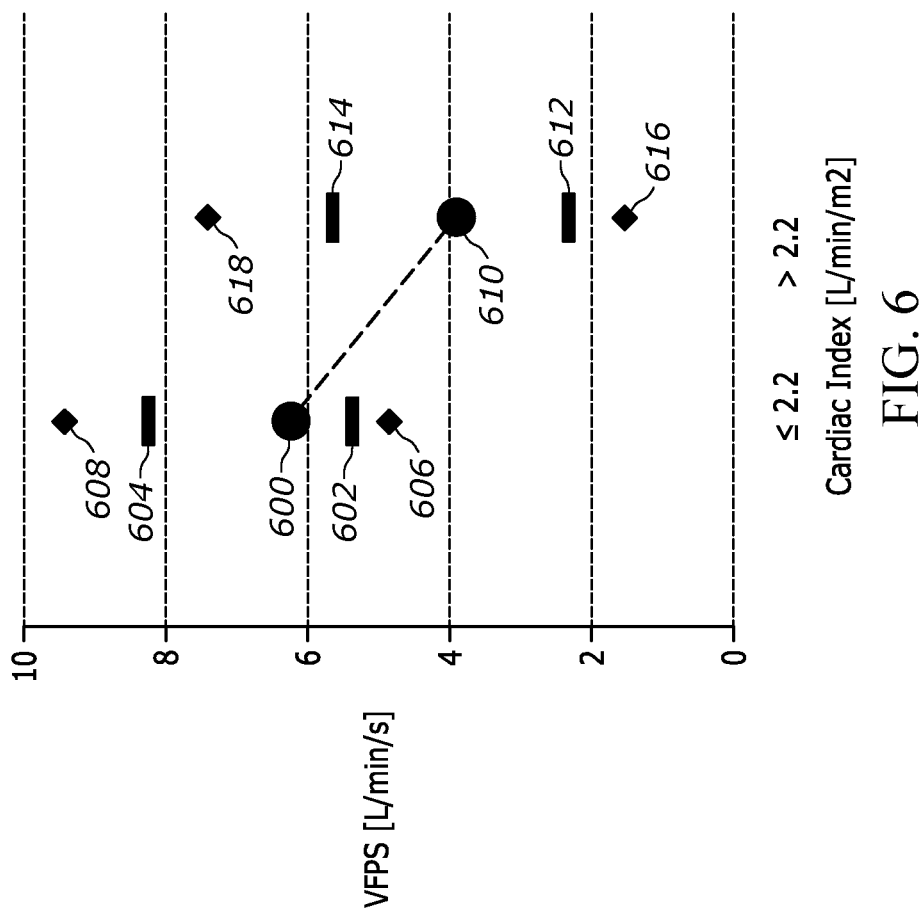
FIG. 6 shows a whisker plot of ventricular filling phase slope versus cardiac index in accordance with an illustrative embodiment.

Referring to FIG. 6, a whisker plot of ventricular filling phase slope versus CI≤2.2 L/min/m² and CI>2.2 L/min/m² is shown in accordance with an illustrative embodiment. It was determined that VFPS was significantly higher in patients with a CI≤2.2 L/min/m² than in patients with a CI>2.2 L/min/m² (7.4±1.8 L/min/s vs. 4.8±2.0 L/min/s, p=0.002). The VFPS values for CI≤2.2 L/min/m² shown in FIG. 6 include a median VFPS value 600, a lower quartile VFPS value 602, an upper quartile VFPS value 604, a lower decile VFPS value 606, and an upper decile VFPS value 608. The VFPS values for CI>2.2 L/min/m² shown in FIG. 6 include a median VFPS value 610, a lower quartile VFPS value 612, an upper quartile VFPS value 614, a lower decile VFPS value 616, and an upper decile VFPS value 618.

Figure 7:
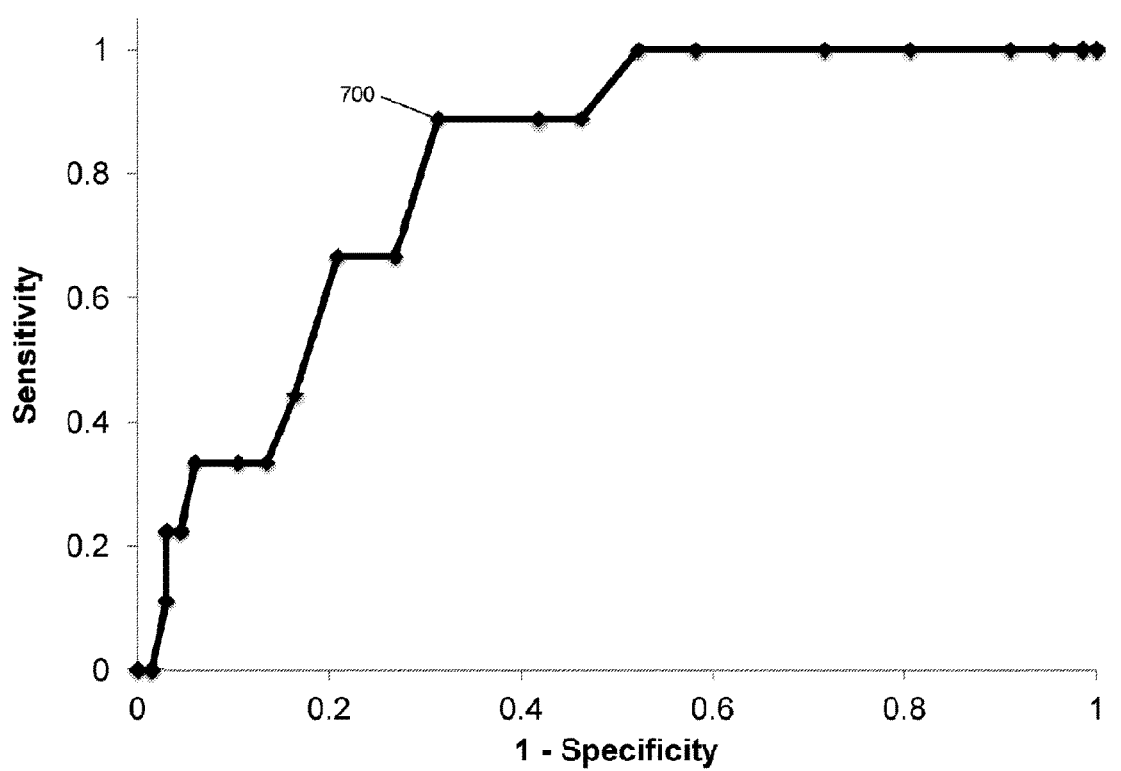
FIG. 7 shows a receiver operating characteristic curve for using a ventricular filling phase slope value to predict a cardiac index less than 2.2 L/min/m$^2$ in accordance with an illustrative embodiment.

Referring to FIG. 7, a receiver operating characteristic curve for using VFPS to predict CI≤2.2 L/min/m² is shown in accordance with an illustrative embodiment. A ventricular filling phase slope threshold 700 (threshold value TCI) of 5.0 L/min/s predicted a CI ≤2.2 L/min/m² with a sensitivity of 89% and specificity of 69% (AUC=0.83).

The receiver operating characteristic curves of FIG. 6 and FIG. 7 were generated by determining true positive rates, false positive rates, true negative rates, and false negative rates for a given VFPS to detect PCWP≥18 mmHg and CI≤2.2 L/min/m², respectively. Sensitivity and specificity were calculated from the above information for each VFPS threshold ranging from 0 to 11. The receiver operating characteristic curves are a plot of sensitivity vs. 1—specificity for all possible thresholds. Specific threshold values may vary based on the test data used.

In operation 228, a warning is triggered indicating that a low value of CI is statistically likely based on the threshold value $T_{CI}$. For example, a message may be stored in computer-readable medium 112 as data 130, presented on display 122, printed on printer 126, and/or issued as an audible warning through speaker 124.

In operation 230, other flow/pressure parameters may be computed from the received flow rate data. In an operation 232, one or more operating parameters of VAD 104 may be modified based on the computed parameters, the determined VFPS, the computed average VFPS, etc. For example, a speed of the impeller of VAD 104 may be adjusted, for example, through generation of a pump motor command signal.

In an operation 234, any modified parameters may be sent to VAD 104. In an operation 236, the computed values may be stored as data 130 for future computations and/or for subsequent review.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" in the detailed description is intended to include "and/or" unless specifically indicated otherwise. The illustrative embodiments may be implemented as a method, apparatus, or article of manufacture using standard programming and/or engineering techniques to produce software, firmware, hardware, or any combination thereof to control a computer to implement the disclosed embodiments.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated.

What is claimed is:

1. A non-transitory computer-readable medium having stored thereon computer-readable instructions that when executed by a computing device cause the computing device to:
   compute a threshold value based on a correlation between a pulmonary capillary wedge pressure and a ventricular filling phase segment measured for a plurality of patients using a receiver operating characteristic curve computed based on predicting a predefined value for the pulmonary capillary wedge pressure from the measured ventricular filling phase segment;
   receive flow rate values describing a blood flow rate through a ventricular assist device for a patient;
   identify a ventricular filling phase segment for the patient from a portion of the received flow rate values;
   determine a slope of the received flow rate values during the identified ventricular filling phase segment;
   compare the determined slope to the computed threshold value; and
   when the determined slope exceeds the computed threshold value based on the comparison, trigger a warning regarding an elevated pulmonary capillary wedge pressure.

2. The non-transitory computer-readable medium of claim 1, wherein the computed threshold value is 5.8 liters per minute per second.

3. The non-transitory computer-readable medium of claim 1, wherein the computed threshold value is selected to predict that the pulmonary capillary wedge pressure is greater than or equal to a predetermined pressure threshold.

4. The non-transitory computer-readable medium of claim 3, wherein the predetermined pressure threshold is 18 millimeters mercury.

5. The non-transitory computer-readable medium of claim 1, wherein the computer-readable instructions further cause the computing device to:
   compute a second threshold value based on a second correlation between a cardiac index and the ventricular filling phase segment measured for the plurality of patients using a second receiver operating characteristic curve computed based on predicting a predefined value for the cardiac index from the measured ventricular filling phase segment;
compare the determined slope to the computed second threshold value; and
when the determined slope exceeds the computed second threshold value based on the comparison, trigger a second warning regarding a low cardiac index value.

6. The non-transitory computer-readable medium of claim 5, wherein the computed second threshold value is 5.0 liters per minute per second.

7. The non-transitory computer-readable medium of claim 5, wherein the computed second threshold value is selected to predict that the cardiac index is greater than or equal to a predetermined index threshold.

8. The non-transitory computer-readable medium of claim 7, wherein the predetermined index threshold is 2.2 liters per minute per square meter.

9. A method of providing a warning regarding a heart status, the method comprising:
computing, by a computing device, a threshold value based on a correlation between a pulmonary capillary wedge pressure and a ventricular filling phase segment measured for a plurality of patients using a receiver operating characteristic curve computed based on predicting a predefined value for the pulmonary capillary wedge pressure from the measured ventricular filling phase segment;
receiving, by the computing device, flow rate values describing a blood flow rate through a ventricular assist device for a patient;
identifying, by the computing device, a ventricular filling phase segment for the patient from a portion of the received flow rate values;
determining, by the computing device, a slope of the received flow rate values during the identified ventricular filling phase segment;
comparing, by the computing device, the determined slope to the computed threshold value; and
when the determined slope exceeds the computed threshold value based on the comparison, triggering, by the computing device, a warning regarding an elevated pulmonary capillary wedge pressure.

10. The method of claim 9, wherein the computed threshold value is 5.8 liters per minute per second.

11. The method of claim 9, wherein the computed threshold value is selected to predict that the pulmonary capillary wedge pressure is greater than or equal to a predetermined pressure threshold.

12. The method of claim 11, wherein the predetermined pressure threshold is 18 millimeters mercury.

13. The method of claim 9, further comprising:
computing, by the computing device, a second threshold value based on a second correlation between a cardiac index and the ventricular filling phase segment measured for the plurality of patients using a second receiver operating characteristic curve computed based on predicting a predefined value for the cardiac index from the measured ventricular filling phase segment;
comparing, by the computing device, the determined slope to the computed second threshold value; and
when the determined slope exceeds the computed second threshold value based on the comparison, triggering, by the computing device, a second warning regarding a low cardiac index value.

14. The method of claim 13, wherein the computed second threshold value is 5.0 liters per minute per second.

15. The method of claim 13, wherein the computed second threshold value is selected to predict that the cardiac index is greater than or equal to a predetermined index threshold.

16. The method of claim 15, wherein the predetermined index threshold is 2.2 liters per minute per square meter.

17. A computing device comprising:
a processor; and
a non-transitory computer-readable medium operably coupled to the processor, the computer-readable medium having computer-readable instructions stored thereon that, when executed by the processor, cause the computing device to
compute a threshold value based on a correlation between a pulmonary capillary wedge pressure and a ventricular filling phase segment measured for a plurality of patients using a receiver operating characteristic curve computed based on predicting a predefined value for the pulmonary capillary wedge pressure from the measured ventricular filling phase segment;
receive flow rate values describing a blood flow rate through a ventricular assist device for a patient;
identify a ventricular filling phase segment for the patient from a portion of the received flow rate values;
determine a slope of the received flow rate values during the identified ventricular filling phase segment;
compare the determined slope to the computed threshold value; and
when the determined slope exceeds the computed threshold value based on the comparison, trigger a warning regarding an elevated pulmonary capillary wedge pressure.

18. The computing device of claim 17, wherein the computed threshold value is selected to predict that the pulmonary capillary wedge pressure is greater than or equal to a predetermined pressure threshold.

19. The computing device of claim 17, wherein the computer-readable instructions further cause the computing device to:
compute a second threshold value based on a second correlation between a cardiac index and the ventricular filling phase segment measured for the plurality of patients using a second receiver operating characteristic curve computed based on predicting a predefined value for the cardiac index from the measured ventricular filling phase segment;
compare the determined slope to the computed second threshold value; and
when the determined slope exceeds the computed second threshold value based on the comparison, trigger a second warning regarding a low cardiac index value.

20. The computing device of claim 19, wherein the computed second threshold value is selected to predict that the cardiac index is greater than or equal to a predetermined index threshold.

* * * * *